(12) United States Patent
Helgen

(10) Patent No.: US 10,674,700 B2
(45) Date of Patent: Jun. 9, 2020

(54) DISTRIBUTION UNIT FOR MILK SAMPLES

(71) Applicant: DELAVAL HOLDING AB, Tumba (SE)

(72) Inventor: Karl Helgen, Tumba (SE)

(73) Assignee: DeLaval Holding AB, Tumba (SE)

( * ) Notice: Subject to any disclaimer, the term of this patent is extended or adjusted under 35 U.S.C. 154(b) by 158 days.

(21) Appl. No.: 15/753,066

(22) PCT Filed: Aug. 17, 2016

(86) PCT No.: PCT/SE2016/050765
§ 371 (c)(1),
(2) Date: Feb. 15, 2018

(87) PCT Pub. No.: WO2017/030495
PCT Pub. Date: Feb. 23, 2017

(65) Prior Publication Data
US 2018/0235171 A1     Aug. 23, 2018

(30) Foreign Application Priority Data
Aug. 20, 2015   (SE) ........................................ 1551083

(51) Int. Cl.
*G01N 33/04*   (2006.01)
*A01J 5/04*   (2006.01)
(Continued)

(52) U.S. Cl.
CPC .............. *A01J 5/045* (2013.01); *A01J 5/0132* (2013.01); *G01N 33/04* (2013.01); *G01N 35/1097* (2013.01)

(58) Field of Classification Search
CPC ...... A01J 5/045; G01N 33/04; G01N 35/1097
See application file for complete search history.

(56) References Cited

U.S. PATENT DOCUMENTS

| | | | | |
|---|---|---|---|---|
| 4,041,385 A | * | 8/1977 | Gulliford | ............. G01N 1/2035 324/71.1 |
| 2005/0217351 A1 | * | 10/2005 | Kreck | ...................... G01N 1/16 73/64.56 |

(Continued)

FOREIGN PATENT DOCUMENTS

| WO | 2004/111613 A1 | 12/2004 |
|---|---|---|
| WO | 2005/020674 A1 | 3/2005 |

(Continued)

OTHER PUBLICATIONS

International—Type Search Report, dated Mar. 16, 2016, from corresponding priority national application No. 1551083-7.
(Continued)

*Primary Examiner* — Jamel E Williams
(74) *Attorney, Agent, or Firm* — Young & Thompson

(57) ABSTRACT

A distribution unit for milk samples includes a flow passage, a valve controlled milk inlet port through which milk is delivered to the flow passage, a pump port through which a sampling pump communicates with the flow passage, and at least two valve controlled milk sampling outlet ports through which milk samples are delivered from the flow passage to a respective milk sample analyzing unit. The flow passage has a longitudinal extension between a first end and a second end, and the milk sampling outlet ports are connected to the flow passage in positions located between the connection position of the milk inlet port and the connection position of the pump port.

11 Claims, 3 Drawing Sheets

(51) Int. Cl.
*A01J 5/013* (2006.01)
*G01N 35/10* (2006.01)

(56) References Cited

U.S. PATENT DOCUMENTS

| 2011/0132264 A1* | 6/2011 | Akerman | A01J 5/0134 |
| | | | 119/14.08 |
| 2013/0247692 A1* | 9/2013 | Gudmundsson | G01N 1/10 |
| | | | 73/863.02 |

FOREIGN PATENT DOCUMENTS

| WO | 2012/087235 A1 | 6/2012 |
| WO | 2013/032397 A1 | 3/2013 |

OTHER PUBLICATIONS

International Search Report, dated Oct. 28, 2016, from corresponding PCT application No. PCT/SE2016/050765.

* cited by examiner

DISTRIBUTION UNIT FOR MILK SAMPLES

THE BACKGROUND OF THE INVENTION AND PRIOR ART

The present invention relates to a distribution unit for milk samples, wherein the distribution unit comprises a flow passage, a valve controlled milk inlet port through which milk is delivered to the flow passage, a pump port through which a sampling pump communicates with the flow passage, and at least two valve controlled milk sampling outlet ports through which milk samples are delivered from the flow passage to a respective milk sample analyzing unit.

The milk from an animal milked in a milking place is usually connected in a local milk receiver. When a milking operation has been finished, a milk pump feeds the milk from the milk receiver to a common milk tank collecting milk from several animals. From the milk tank, the milk may then be delivered to the dairy industry for further processing. Before or during feeding of the milk to the milk tank, milk samples may be taken of the milk from the individual animals. The milk samples may be taken for different tests regarding the quality of the milk, such as the content of fat, protein, lactose and the quantity of microorganisms (somatic cell counting).

WO 2013/032397 shows a sampling device comprising a housing enclosing an inner space having a determined volume and configured to house a determined quantity of milk. An inlet conduit is connected to the inner space for supplying milk to the inner space. An output device is connected to the inner space and configured to output said determined quantity from the inner space. The output device comprises a distributor comprising a plurality of outlet passages. The milk sampling device comprises a forcing member operable in the inner space to force, in an output operation, the milk in the inner space to the distributor and through at least one of the outlet passages.

SUMMARY OF THE INVENTION

An object of the present invention is to provide a distribution unit for milk samples by which a plurality of milk samples can be taken in a reliable and convenient manner at substantially the same time and with a simple design which easily can be adapted to an arbitrary number of outlets for milk samples. Further objects are to provide a distribution unit including few components, which allow a simple conduit routing and which are easy to manufacture.

These objects are achieved by the distribution unit of the kind initially defined which is characterized in that the flow passage has a longitudinal extension between a first end and a second end, and that said milk sampling outlet ports are connected to the flow passage in positions located between the connection position of the milk inlet port and the connection position of the pump port. Such a design makes it possible to draw a determined quantity of milk with a great accuracy from the milk inlet port, via the flow passage and the pump port, to the sampling pump. The determined quantity of milk may then be delivered back by the sampling pump to the flow passage and to one or several of the milk sample analyzing unit via one or several of the milk sampling outlet ports which are connected to the flow passage. Such a flow passage may be relatively narrow and it requires a relatively small space. Furthermore, it is relatively easy to change the length of the distribution unit and the flow passage in order to vary the number of milk sampling outlet ports connected to the flow passage.

According to an embodiment of the invention, the milk inlet port is arranged in the vicinity of the first end of the flow passage and the pump port is arranged at the vicinity of the opposite second end of the flow passage. In this case, the entire flow passage is used for conducting milk from the milk inlet port, via the milk sampling outlet ports, to the pump port. Preferably, the ports are arranged in a row on the distribution unit. Such an arrangement of the ports results in a simple conduit routing to the distribution unit.

According to an embodiment of the invention, the distribution unit comprises a valve controlled washing liquid inlet port delivering washing liquid to the flow passage. The existence of such a port makes it easy to supply a washing liquid to the flow passage and distribute the washing liquid to all flow surfaces in the distribution unit, the conduits connected to the distribution unit and the sampling pump. The distribution unit may comprise a valve controlled compressed air inlet port delivering compressed air to the flow passage. The existence of such a port makes it easy to supply compressed air to the flow passage and distribute the compressed air to all flow surfaces in the distribution unit, the conduits connected to the distribution unit and the sampling pump. The compressed air may be used to remove milk residues from the flow surfaces or perform a drying process after a washing process with washing liquid.

According to an embodiment of the invention, a bleed valve is arranged at the first end of the flow passage. The bleed valve may be arranged close to an opening of the milk inlet port. Preferably, the bleed valve is a part of a double bleed block having a block bleed block function. In this case, the bleed valve may be arranged between a sample valve in the milk conduit and a valve body in the distribution unit. The bleed block is a safety system. In case the sample valve in the milk conduit leaks, the bleed valve can direct out the leaking milk from the distribution unit. In case the valve body in the distribution unit leaks during a washing process, the bleed valve can direct out leaking washing liquid from the distribution unit. A drain valve may be arranged at the second end of the flow passage. The drain valve leads out milk which has been used to remove milk residues from a previous milk sample from the flow surfaces in the distribution unit and the pump before a milk sample is taken. The drain valve also leads out washing liquid and/or compressed air after a washing process of the distribution unit.

According to an embodiment of the invention, the distribution unit comprises valve bodies controlling the flow through the valve controlled ports and control valves controlling the movement of the valve bodies between an open position and a closed position. All valve bodies and the control valves may have the same design and be arranged in a row in the distribution unit. Such a distribution unit may be compact and it includes easily replaceable components.

According to an embodiment of the invention, the distribution unit comprises a plate-shaped elastic gasket having a first side designed to form a side surface of the flow passage and an opposite second side surface to be in contact with the valve bodies. During movement of an individual valve body to the closed position, it displace a part of the elastic gasket to a position in which said part comes in contact with and closes an opening of a port to the flow passage. The elastic properties of the gasket facilitate such a movement and a sealed closing of the opening. Components which are used in contact with milk and are manufactured of certain materials such as rubber and elastomers are to be replaced at regular intervals. In this case, a gasket in one piece is used for all valve bodies. Consequently, it is a very simple action to replace a worn-out gasket with a new one.

According to an embodiment of the invention, the distribution unit comprises a first block element including the ports and the flow passage. Such a block element may be an elongated material body with a longitudinal recess defining the flow passage and transverse holes defining the ports. The distribution unit may comprise a second block element enclosing the valve bodies. The second block element may be an elongated material body designed with a number of spaces for reception of a respective valve body. The distribution unit may comprise a third block element supporting the control valves. The third block element may be an elongated material body comprise channels supplying two different control pressures to the control valves. The control valve may be arranged in a row on a side surface of the third block element. The block elements may be manufactured by injection moulding of a suitable plastic material. The block element may be stacked on each other in a connected state.

According to an embodiment of the invention, the control valves are 3/2 valves allowing supply of two different control pressures to the valve bodies. 3/2 valves such as 3/2 solenoids valves have a simple designed and are relatively inexpensive to produce. The valve bodies may be moved to the closed position by the action of a respective valve spring. In this case, the valve bodies may be moved to the open position when the control valve supplies the higher control pressure to the valve bodies.

BRIEF DESCRIPTION OF THE DRAWINGS

The present invention is now to be explained more closely by means of a preferred embodiment which is disclosed as an example and with reference to the attached drawings.

BRIEF DESCRIPTION OF A PREFERRED
EMBODIMENT OF THE INVENTION

Figure 1:
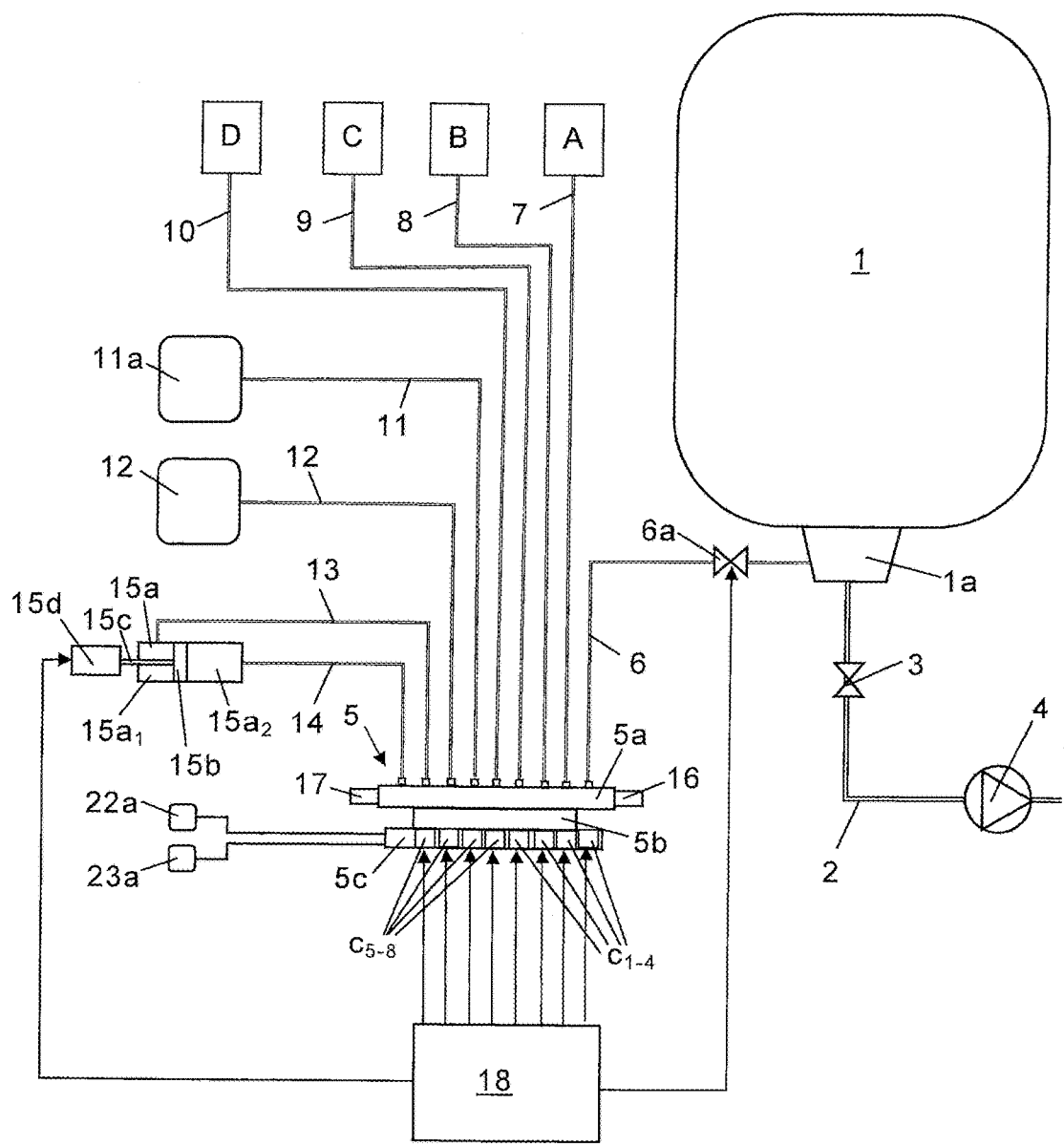
FIG. 1 shows a milk sampling device including a distribution unit according to the invention.
Figure 2:
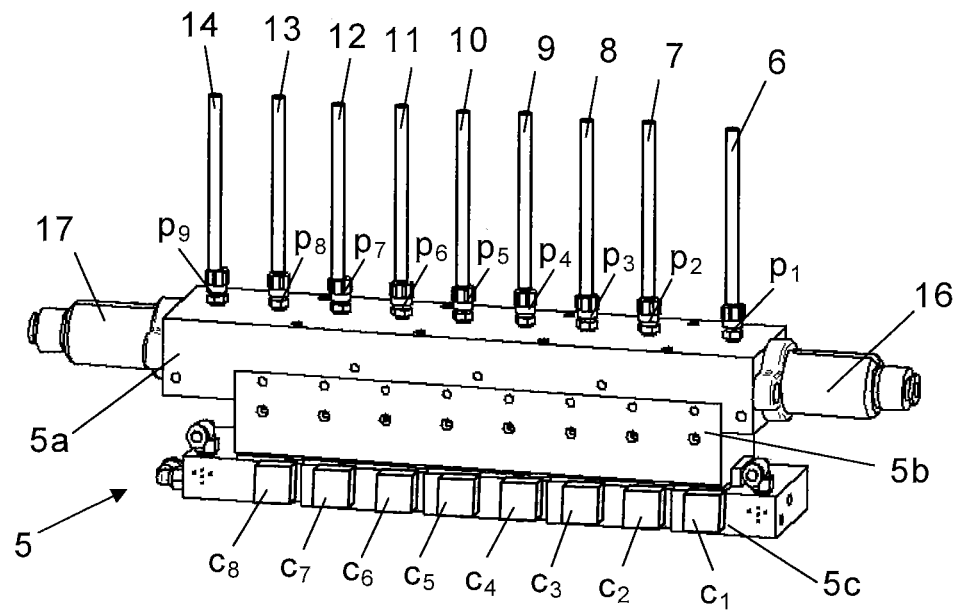
FIG. 2 shows a perspective view of the distribution unit.

FIG. 1 shows a milk receiver 1 collecting milk from animals milked by, for example, a voluntary robotic milking system. A milk line 2 is connected to a bottom portion 1a of the milk receiver 1. The milk line 2 comprises a valve 3 and a milk pump 4. When the valve 3 is in an open position and the pump 4 is activated, milk is pumped from the milk receiver 1, via the milk line 2, to a not shown milk tank collecting milk from several milking operations. A milk sampling device is configured to take milk samples of the milk in the milk receiver 1 before it is fed to the milk tank. The milk sampling device comprises a distribution unit 5. FIG. 2 shows the distribution unit 5 more in detail. The distribution unit 5 comprises a first block element 5a, a second block element 5b and a third block element 5c which are stacked on each other in a connected state. The second block 5b is arranged in position between the first element 5a and the third element 5c. The block elements 5a-c form a housing in a connected state. Each block element 5a-c may be formed of an injection moulded plastic material.

The first block element 5a comprises a plurality of ports $p_{1-9}$ for connection of conduits 6-14. The ports $p_{1-9}$ are arranged in a straight row on a side of the first block element 5a facing away from the second block element 5b. A milk conduit 6 extends between the bottom portion 1a of the milk receiver 1 and a milk inlet port which is defined as a first port $p_1$. The first port $p_1$ is an end port of the row of ports $p_{1-9}$. The milk conduit 6 is provided with a sample valve 6a by which the milk flow from the milk receiver 1 to the distribution unit 5 is controlled. In this case, the sample valve 6a is a component in the milk conduit but it is possible to integrate the sample valve 6a in the distribution unit 5. A first milk sampling conduit 7 extends between a first milk sample analyzing unit A and a first milk sampling outlet port which is defines as a second port $p_2$. A second milk sampling conduit 8 extends between a second milk sample analyzing unit B and a second milk sampling outlet port which is defines as a third port $p_3$. A third milk sampling conduit 9 extends between a third milk sample analyzing unit C and a third milk sampling outlet port which is defines as a fourth port $p_4$. A fourth milk sampling conduit 10 extends between a fourth milk sample analyzing unit D and a fourth milk sampling outlet port which is defines as a fifth port $p_5$. The milk sample analyzing units A-D may be used to take different tests of milk. In the embodiment disclosed, four such tests can be used, but it is to be noted that distribution unit 5 can be associated with more or less than four milk sample analyzing units A-D. The milk sample analyzing units A-D can include equipment for analyzing of the milk samples on site. Alternatively, the milk samples are collected on site in samples containers before they are transported to a laboratory or the like where the milk samples are analyzed.

A washing liquid conduit 11 extends between a washing liquid source 11a and a washing liquid inlet port which is defined as a sixth port $p_6$. A compressed air conduit 12 extends between a compressed air source 12a and a compressed air inlet port which is defined as a seventh port $p_7$. The milk sampling device comprises a sampling pump 15 connected to the distribution unit 5. The sampling pump 15 comprises a cylindrical housing 15a having an inner space divided in a first chamber $15a_1$ and a second chamber $15a_2$ by a movably arranged piston 15b. The piston 15b is, via a piston rod 15c, connected to an actuator 15d. The actuator 15d may be realized as electric, pneumatic or hydraulic motor, for instance an electric step motor. A first pump conduit 13 extends between the first chamber $15a_1$ of the sampling pump 15 and a first pump port which is defined as an eight port $p_8$. A second pump conduit 14 extends between the second chamber $15a_2$ of the sampling pump 15 and a second pump port which is defined as a ninth port $p_9$. The ninth port $p_9$ is a second end port of the row of ports $p_{1-9}$ arranged on the first block element 5a. The first block element 5a comprises a bleed valve 16 arranged on a first end surface of the first block element 5a. The bleed valve 16 is arranged in a position close to the first port $p_1$. The first block element 5a comprises a drain valve 17 arranged on an opposite second end surface of the first block element 5a in a position close to the ninth port $p_9$. The third block element 5c supports control valves $c_{1-8}$ controlled by a control unit 18.

Figure 3:
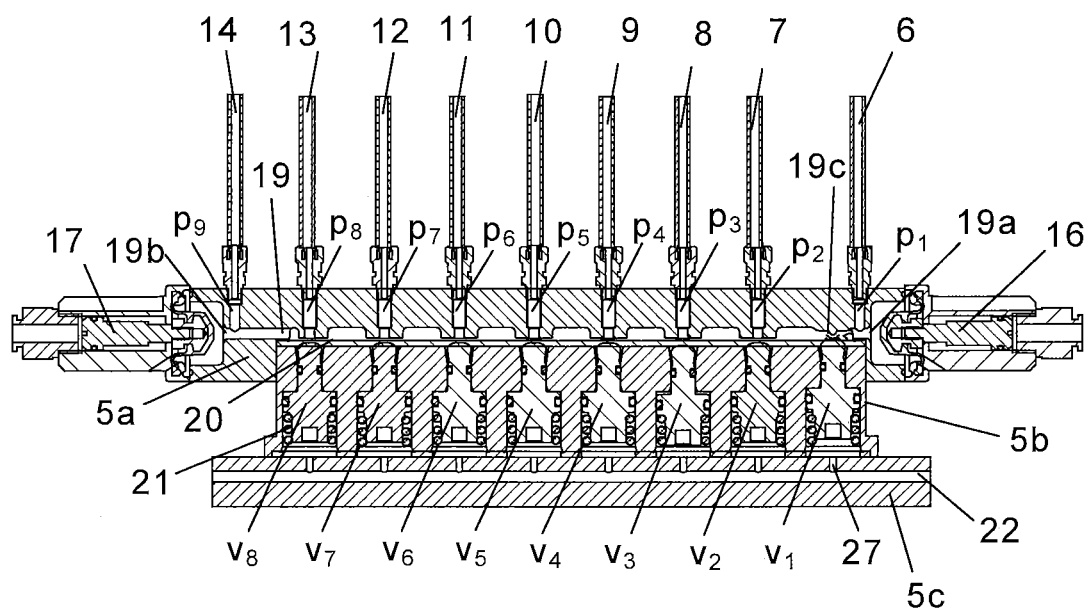
FIG. 3 shows longitudinal sectional view the distribution unit.

FIG. 3 shows a longitudinal sectional view of the distribution unit 5. Each port is configured to receive an end portion of a conduit 6-14. Each port $p_{1-9}$ comprises an opening to a flow passage 19 in the first block element 5a. The flow passage 19 extends in a longitudinal direction of the first block element 5a between a first end 19a and a second end 19b. The bleed valve 16 is arranged at the first end 19a of the flow passage 19 and the drain valve 16 is arranged at the second end surface 19b of the first block element 5a. The first block defines a first longitudinal side surface of the flow passage 19. An opposite longitudinal side surface of the flow passage 19 is defined by an elastic plate-shaped gasket 20. The elastic gasket 20 is arranged in an area located between the first block element 5a and the second block element 5b.

Each intermediate port $p_{2-8}$ in the row of ports $p_{1-9}$ comprises a portion protruding into the flow passage 19 from a longitudinal side surface of the flow passage defined by the first block element 5a. As a consequence, the openings of the intermediate ports $p_{2-8}$ are arranged closer to the elastic gasket 20 than the remaining parts of the side surface defined by the first block element 5a. The flow between the openings of the intermediate ports $p_{2-8}$ and the flow passage 19 is controlled by a respective valve body $v_{2-8}$ arranged in the second block element 5b. The longitudinal side surface defined by the first block element 5a comprises a further protruding portion. The further portion is arranged in a position 19c located between the opening of the first port $p_1$ and the opening of the second port $p_2$. A first valve body $v_1$ is arranged on the opposite side of said protruding portion. The bleeding valve 16 is arranged in a position between the first valve body $v_1$ and the sample valve 6a. The first valve body $v_1$ is a block in a bleed block having a block bleed block function. In case the sample valve 6a leaks, the first valve body $v_1$ blocks the milk flow to the flow passage 19 of the unit 5 and the milk leaves the distribution unit 5 via the bleeding valve 16. In case, first valve body $v_1$ leaks, the medium in the flow passage 19 will be blocked by the sample valve 6a and the medium leaves the distribution unit 5 via the bleeding valve 16. An alternative positioning of the sample valve 6a is in the first port $p_1$ of the distribution unit 5.

The second block element 5b comprises inner spaces receiving a respective valve body $v_{1-8}$. Each valve body $v_{1-8}$ is movably arranged in the respective inner space of the second block element 5b between a closed position and an open position. In the closed position, a front portion of the valve bodies $v_{1-8}$ act with a force on the elastic gasket 20 such that the elastic gasket 20 closes the openings of the ports $p_{2-8}$ or the flow passage in the position 19c. A valve spring 21 exerts a force on each valve body $v_{1-8}$ towards the closed position.

Figure 4:
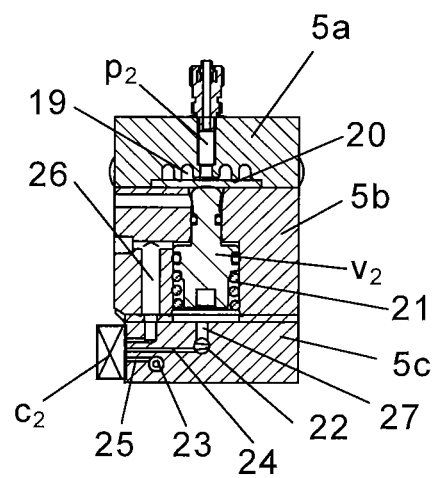
FIG. 4 shows a transverse sectional view of the distribution unit and FIG. 5 shows a longitudinal sectional view of the first block element of the distribution element.

FIG. 4 shows a transverse sectional view of a part of the distribution unit 5 comprising the second valve body $v_2$. However, all valve bodies $v_{1-8}$ have the same design as the second valve body $v_2$. The third block element 5c comprises a first longitudinal channel 22 connected to an ambient air source 22a and a second longitudinal channel 23 connected to a compressed air source 23a. A plurality of first transverse channels 24 extends between the first longitudinal channel 22 and a respective opening in a side surface of the third block element 5c. A plurality of second transverse channels 25 extends between the second longitudinal channel 23 and a respective opening in the same side surface of the third block element 5c. A plurality of transverse control channel 26 extends between an upper part of the inner space of the respective valve body $v_{1-8}$ and a respective opening in the side surface of the third block element 5c. Furthermore, the second block element 5b comprises transverse channels 27 extending between the first longitudinal channel 22 and a lower part of the inner space for the respective valve body $v_{1-8}$. As a consequence, the lower parts of the inner space for the valve bodies $v_{1-8}$ contain permanently air at ambient pressure.

Each control valve $c_{1-8}$ is 3/2 valve which may be a 3/2 solenoid valve. Each control valve $c_{1-8}$ comprises a first inlet port in contact with the first transverse channel 24, a second inlet port in contact with the second transverse channel 25 and an outlet port in contact with the control channel 26. When the control unit 18 sets the control valves $c_2$ in a first position, the control valve $c_2$ connects the first transverse channel 24 to the control channel 26. The upper part of the inner space receives a control pressure in the form of ambient pressure from the first longitudinal channel 22. In this case, the upper part as well as the lower part of the inner space for the valve body $v_2$ contains air at ambient pressure. As a consequence, the valve spring 21 moves the valve body $v_2$ to the closed position. The front portion of the valve body $v_2$ acts on a part the elastic gasket 20 such that it closes the opening of the second port $p_2$. When the control unit 18 sets the control valve $c_2$ in a second position the second transverse channel 25 is connected to the control channel 26. In this case, the upper part of the inner space receives a control pressure in the form of compressed air from the second longitudinal channel 23. The compressed air moves the valve body $v_2$ from the closed position to an open position against the action of the valve springs 21. The front portion of the valve body $v_2$ is retracted and the elastic gasket 20 exposes the opening of the second port $p_2$.

Figure 5:
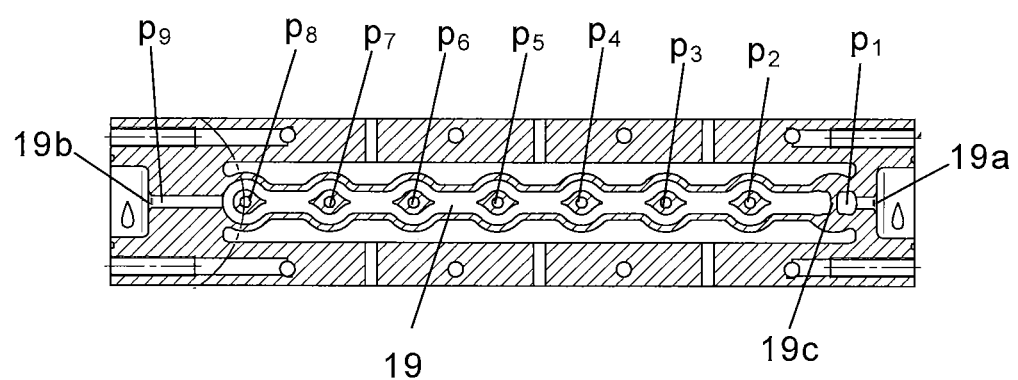

FIG. 5 shows an elongated sectional view of the first block element 5a. The elongated flow passage 19 is here indicated more in detail and the positions of the ports $p_{1-9}$ in relation to the flow passage 19.

In case a milk sample is to be taken, the milk is mixed with a stirring member in the milk receiver 1 to a homogenous composition. Initially, all valve bodies $v_{1-8}$ are in a closed position. The control unit 18 starts to provide a rinsing process of the flow surfaces of the distribution unit 5 and the sampling pump 15. The control unit 18 opens the sample valve 6a and sets the first control valve $c_1$ in the second position. As a result, the first body valve $v_1$ is moved from the closed position to the open position. The flow passage 19 in the position 19c is open and flow communication is created between the milk conduit 6 and the entire flow passage 19. The control unit 18 activates the actuator 15d such that it moves the piston 15b from an initial position in which the second chamber $15a_2$ has a minimal size. The movement of the piston 15 expands the second chamber $15a_2$ and a vacuum pressure is created in the second chamber $15a_2$, the second pump conduit 14, the flow passage 19 and the milk conduit 6.

When the piston has reached a determined position and the second chamber $15a_2$ has received a determined quantity of milk, the control unit 18 sets the first control valve $c_1$ in the first position such that the first body valve $v_1$ is moved to the closed position. The milk flow from the milk conduit 6 to the flow passage 19 ceases. The control unit 18 activates the actuator 15d such that it moves the piston 15b in a direction back towards the initial position. This movement of the piston 15b provides a milk flow from the second chamber $15a_2$, via the second pump line 14 and the ninth port $p_9$, to the flow passage 19. All valve bodies $v_{1-8}$ are in the closed position and the pressure increases in the flow passage 19. The drainage valve 17 opens and the milk leaves the flow passage 19 via the drainage valve 17. This initial milk flow to the distribution unit 5 cleans the inner surfaces of the distribution unit 5 from milk residues from a previous milk sample. When the piston 15b has reached the initial position, the second chamber $15a_2$ of the pump 15 has been emptied of rinsing milk.

Then the milk sampling process starts. The control unit 18 again sets the first control valve $c_1$ in the second position and the first body valve $v_1$ is moved to the open position such that the flow passage 19 is open in the position 19c. The control unit 18 activates the actuator 15d which moves the piston 15b from the initial position. The second chamber $15a_2$ expands and a vacuum pressure is created in the second pump conduit 14, the flow passage 19 and the milk conduit 6 which provides a milk flow from the milk conduit 6 to the second chamber $15a_2$. When the second chamber $15a_2$ has received a determined quantity of milk, the control unit 18 sets the first control valve $c_1$ in the first position such that the first body valve $v_1$ is closed. The determined quantity of milk, now contained in the second chamber $15a_2$, or a part of the determined quantity of milk, may then be delivered to any one of the milk analysing units A-D, for instance the first milk analysing unit A. In this case, the control unit 18 sets the second control valve $c_2$ in the second position such that the second valve body $v_2$ is moved to the open position in which the opening of the second port $p_2$ is exposed.

The control unit 18 activates the actuator 15d such that it moves the piston 15b in the direction towards the initial position. The piston 15b provides a milk flow from the second chamber $15a_2$, via the second pump line 14, the ninth port $p_9$, the flow passage 19, the ninth port $p_9$ and the first analyzing conduit 7, to the first analyzing unit A. It should be noted that the determined quantity of milk contained in second chamber $15a_2$ could be supplied to more than one of the milk analysing conduits 7-10 and thus be distributed to several of the milk analysing units A-D.

The distribution unit 5 and the milk sampling conduits 7-10 are to be washed with regular intervals. When a washing process is to be performed, the control unit 18 sets the sixth control valve $c_6$ in the second position such that the sixth valve body $v_6$ is moved to an open position, Washing liquid is supplied from the washing liquid source 11b, via the washing liquid conduit 11 and the sixth port $p_6$, to the flow passage 19. After that, the control unit 18 may set one or several of the control valves $c_{2-5}$ in the second position and the corresponding valve body $v_{2-5}$ in an open position in order to provide a washing liquid flow through one or several of the ports $p_{2-5}$ and the milk sample analyzing conduits 7-10. The washing liquid flow ceases when the control unit 18 sets the sixth control valve $c_6$ in the first position such that the sixth valve body $v_6$ is moved to the closed position. Thereafter, the control unit 18 may set the seventh control valve $c_7$ in the second position such that the seventh valve body $v_7$ is moved to the open position. Compressed air is supplied from the compressed air source 12b, via the compressed air conduit 12, the seventh port $p_7$ and the flow passage 19, to the milk sample analyzing conduits 7-10. The compressed air may be supplied in order to dry the inner surfaces of the distribution unit 5 and the milk sample analyzing conduits 7-10 after a washing process with washing liquid. Alternatively, compressed air of a relatively high pressure may be used to clean the inner surfaces of the distribution unit 5 and the milk sample analyzing conduits 7-10 from milk residues.

It is in a corresponding manner possible to supply and wash the pump conduits 13, 14 and the chambers $15a_1$, $15a_2$ 15 and the piston 15b of the pump 15 with washing liquid and/or compressed air. The used washing liquid and the compressed air leave the distribution unit 5 via the drain valve 17.

The invention is not restricted to the described embodiment but may be varied freely within the scope of the claims.

The invention claimed is:

1. A distribution unit (5) for milk samples, comprising:
a first block element having a flow passage (19) defined by a first end (19a), an opposite second end (19b), and a longitudinal extension running therebetween, the longitudinal extension having a plurality of ports extending transversally from the longitudinal extension and each in fluid communication with the flow passage;
a second block element, attached to the first block element and comprising a plurality of spaces; and
a plate-shaped elastic gasket (20) having a first side that forms a longitudinal side surface of the flow passage (19) of the first block element and a second opposite side in contact with valve bodies located in the spaces of the second block element,
a first of said plurality of ports constituted by a valve controlled milk inlet port ($p_1$) through which milk is delivered to the flow passage (19),
a second of said plurality of ports constituted by a pump port ($p_9$) through which a sampling pump communicates with the flow passage (19), and
a third and fourth of said plurality of ports constituted by, respectively, two valve controlled milk sampling outlet ports through which milk samples are delivered from the flow passage (19) to respective milk sample analyzing units,
wherein said milk sampling outlet ports are connected to the flow passage (19) in positions located between the connection position of the milk inlet port ($p_1$) and the connection position of the pump port ($p_9$).

2. The distribution unit according to claim 1, wherein the milk inlet port ($p_1$) is arranged at the first end (19a) of the flow passage (19) and the pump port ($p_9$) is arranged at the opposite second end (19b) of the flow passage (19).

3. The distribution unit according to claim 1, wherein all of the plurality of ports are arranged in a row along a length of the first block element between the first end and the second end.

4. The distribution unit according to claim 1, wherein a fifth of said plurality of ports constituted by a valve controlled washing liquid inlet port configured for delivering washing liquid into the flow passage (19).

5. The distribution unit according to claim 1, wherein a sixth of said plurality of ports constituted by a valve controlled compressed air inlet port configured for delivering compressed air into the flow passage (19).

6. The distribution unit according to claim 1, wherein the first end of the flow passage (19) comprises a bleed valve (16).

7. The distribution unit according to claim 6, wherein the bleed valve (16) is a part of a bleed block connected to said first block element.

8. The distribution unit according to claim 1, wherein the second end of the flow passage (19) comprises a drain valve (17).

9. The distribution unit according to claim 1, wherein at least one of said first block element and said second block element is formed of an injection moulded plastic material.

10. A distribution unit (5) for milk samples, comprising:
a first block element having a flow passage (19) defined by a first end (19a), an opposite second end (19b), and a longitudinal extension running therebetween, the longitudinal extension having a plurality of ports extending transversally from the longitudinal extension and each in fluid communication with the flow passage; and
a second block element, attached to the first block element and comprising a plurality of spaces,
a first of said plurality of ports constituted by a valve controlled milk inlet port ($p_1$) through which milk is delivered to the flow passage (19), a second of said plurality of ports constituted by a pump port ($p_9$) through which a sampling pump communicates with the flow passage (19), and a third and fourth of said plurality of ports constituted by, respectively, two valve controlled milk sampling outlet ports through which milk samples are delivered from the flow passage (19) to respective milk sample analyzing units, wherein said milk sampling outlet ports are connected to the flow passage (19) in positions located between the connection position of the milk inlet port ($p_1$) and the connection position of the pump port ($p_9$), and wherein the control valves are 3/2 valves allowing supply to one of said two different control pressures to the valve bodies.

11. A distribution unit (5) for milk samples, comprising:

a first block element having a flow passage (19) defined by a first end (19*a*), an opposite second end (19*b*), and a longitudinal extension running therebetween, the longitudinal extension having a plurality of ports extending transversally from the longitudinal extension and each in fluid communication with the flow passage; and a second block element, attached to the first block element and comprising a plurality of spaces, a first of said plurality of ports constituted by a valve controlled milk inlet port ($p_1$) through which milk is delivered to the flow passage (19), a second of said plurality of ports constituted by a pump port ($p_9$) through which a sampling pump communicates with the flow passage (19), and a third and fourth of said plurality of ports constituted by, respectively, two valve controlled milk sampling outlet ports through which milk samples are delivered from the flow passage (19) to respective milk sample analyzing units, wherein said milk sampling outlet ports are connected to the flow passage (19) in positions located between the connection position of the milk inlet port ($p_1$) and the connection position of the pump port ($p_9$), and wherein each of the valve bodies are moved to the closed position by the action of a respective valve spring (21).

* * * * *